US012564407B1

(12) United States Patent (10) Patent No.: US 12,564,407 B1
Evyatar et al. (45) Date of Patent: Mar. 3, 2026

(54) REVERSIBLE OCCLUSION DEVICE, SYSTEM AND METHOD

(71) Applicants: Bar Evyatar, Kibbutz Beit Oren (IL); Netta Hirshberg, Givatayim (IL)

(72) Inventors: Bar Evyatar, Kibbutz Beit Oren (IL); Amit Tubishevitz, Tel Aviv (IL); Netta Hirshberg, Givatayim (IL)

(73) Assignees: Bar Evyatar, Kibbutz Beit Oren (IL); Netta Hirshberg, Givatayim (IL)

( * ) Notice: Subject to any disclaimer, the term of this patent is extended or adjusted under 35 U.S.C. 154(b) by 0 days.

(21) Appl. No.: 19/063,464

(22) Filed: Feb. 26, 2025

Related U.S. Application Data

(60) Provisional application No. 63/689,787, filed on Sep. 2, 2024.

(51) Int. Cl.
*A61B 17/12* (2006.01)
(52) U.S. Cl.
CPC .... *A61B 17/1204* (2013.01); *A61B 17/12131* (2013.01)
(58) Field of Classification Search
CPC .......... A61B 17/1204; A61B 17/12131; A61B 17/42; A61F 6/02; A61F 6/20; A61F 6/225; A61F 6/22; A61F 6/146; A61F 6/18
See application file for complete search history.

(56) References Cited

U.S. PATENT DOCUMENTS

| | | | |
|---|---|---|---|
| 3,762,417 | A | 10/1973 | Textor |
| 4,817,602 | A | 4/1989 | Beraha |
| 4,920,982 | A | 5/1990 | Goldstein |
| 6,513,528 | B2 | 2/2003 | Burton et al. |
| 6,852,082 | B2 | 2/2005 | Strickberger et al. |
| 8,132,566 | B2 | 3/2012 | Sokal |
| 8,616,212 | B1 | 12/2013 | Logan |
| 9,247,942 | B2 | 2/2016 | Rudakov et al. |
| 9,597,223 | B2 | 3/2017 | Wijay |
| 10,524,796 | B2 | 1/2020 | Wilson |
| 10,751,124 | B2 | 8/2020 | Eisenfrats et al. |

(Continued)

FOREIGN PATENT DOCUMENTS

| | | |
|---|---|---|
| CA | 3078365 A1 | 4/2019 |
| CA | 3183275 A1 | 11/2021 |

(Continued)

*Primary Examiner* — Ophelia A Hawthorne
(74) *Attorney, Agent, or Firm* — S.J. INTELLECTUAL PROPERTY LTD.

(57) ABSTRACT

A reversible occlusion device configured for being introduced inside a lumen to selectively occlude it, the reversible occlusion device includes a docking unit configured for being docked in the lumen; the docking unit has an upstream end and a downstream end associated with an upstream portion and a downstream portion of the lumen respectively, and an inner volume extending between the ends; the reversible occlusion device further includes at least one restricting element configured for transitioning between a first, closed position, in which it obstructs passage of material across the volume, and a second, open position, in which it allows passage of material across the volume; in both the closed position and the open position, a peripheral portion of the restricting element is in contact with the docking unit; said restricting element is a membrane with a peripheral portion thicker than its central portion.

19 Claims, 14 Drawing Sheets

(56)  References Cited

U.S. PATENT DOCUMENTS

| 11,253,391 | B2 | 2/2022 | Grover et al. |
| 11,318,040 | B2 | 5/2022 | Grover et al. |
| 11,510,807 | B2 | 11/2022 | Grover et al. |
| 11,904,068 | B2 | 2/2024 | Herr et al. |
| 11,951,032 | B2 | 4/2024 | Grover et al. |
| 11,957,616 | B2 | 4/2024 | Grover et al. |
| 2002/0013589 | A1 | 1/2002 | Callister et al. |
| 2007/0163601 | A1 | 7/2007 | Pollock et al. |
| 2008/0302369 | A1 | 12/2008 | Uson Calvo |
| 2012/0192872 | A1* | 8/2012 | Rudakov .......... A61B 17/12104 128/831 |
| 2013/0312762 | A1 | 11/2013 | Wijay et al. |
| 2017/0136143 | A1 | 5/2017 | Herr et al. |
| 2018/0185096 | A1 | 7/2018 | Eisenfrats et al. |
| 2019/0038454 | A1 | 2/2019 | Eisenfrats et al. |
| 2019/0388110 | A1 | 12/2019 | Nguyen et al. |
| 2020/0146876 | A1 | 5/2020 | Grover et al. |
| 2020/0147301 | A1 | 5/2020 | Grover et al. |
| 2022/0015742 | A1 | 1/2022 | Grover et al. |
| 2022/0142812 | A1 | 5/2022 | Grover et al. |
| 2022/0175672 | A1 | 6/2022 | Grover et al. |
| 2022/0313475 | A1 | 10/2022 | Grover et al. |
| 2023/0116862 | A1 | 4/2023 | Grover et al. |
| 2023/0190515 | A1 | 6/2023 | Eisenfrats et al. |
| 2023/0233362 | A1 | 7/2023 | Cohn et al. |
| 2023/0346589 | A1 | 11/2023 | Grover et al. |

FOREIGN PATENT DOCUMENTS

| EP | 3275469 | A1 | 1/2018 |
| EP | 3565484 | B1 | 4/2024 |
| WO | 2015002709 | A1 | 1/2015 |
| WO | 2021035217 | A1 | 2/2021 |
| WO | 2021243046 | A1 | 12/2021 |
| WO | 2024006163 | A3 | 1/2024 |
| WO | 2024086828 | A2 | 4/2024 |
| WO | 2024091496 | A1 | 5/2024 |

* cited by examiner

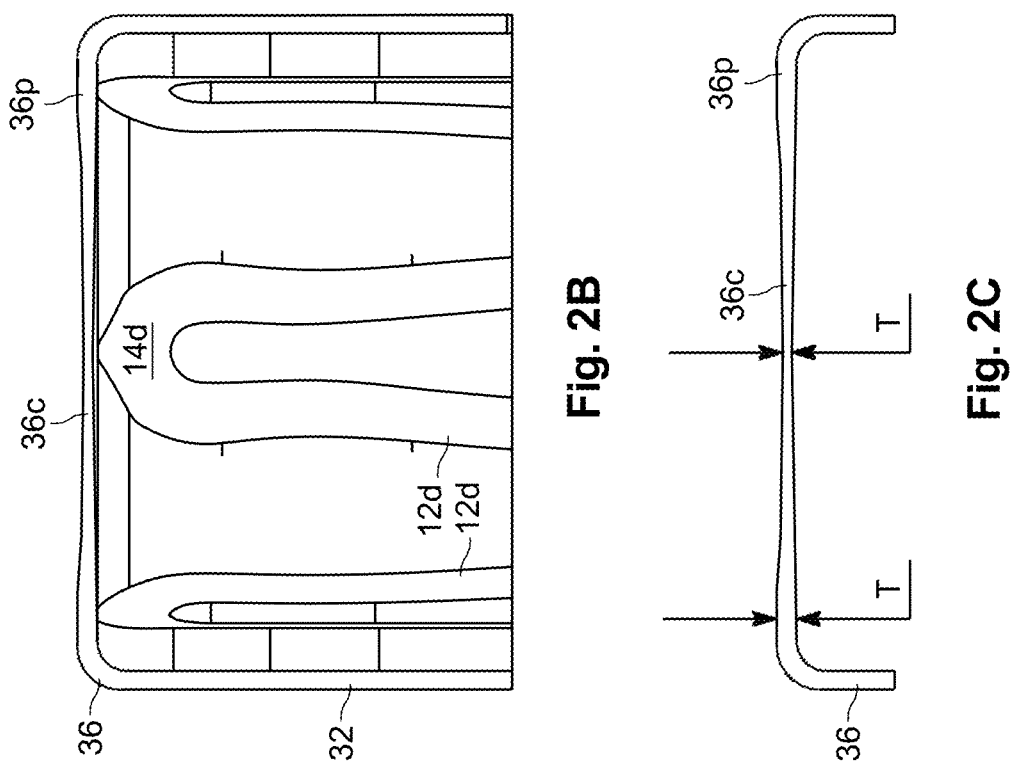
Fig. 2B
Fig. 2C
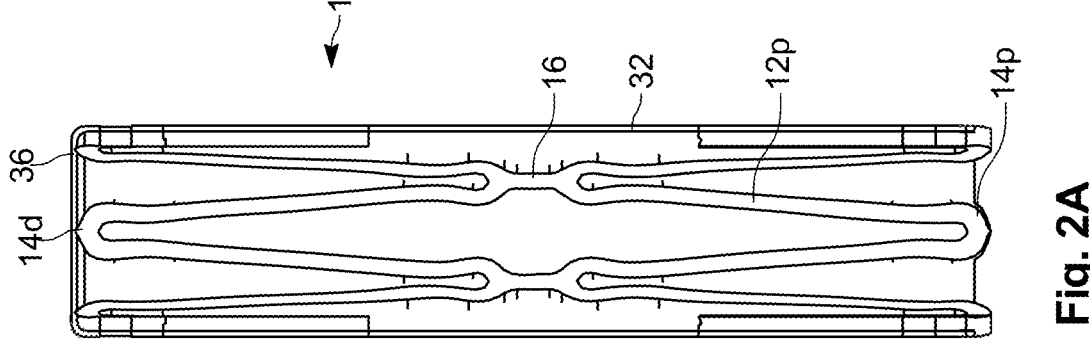
Fig. 2A

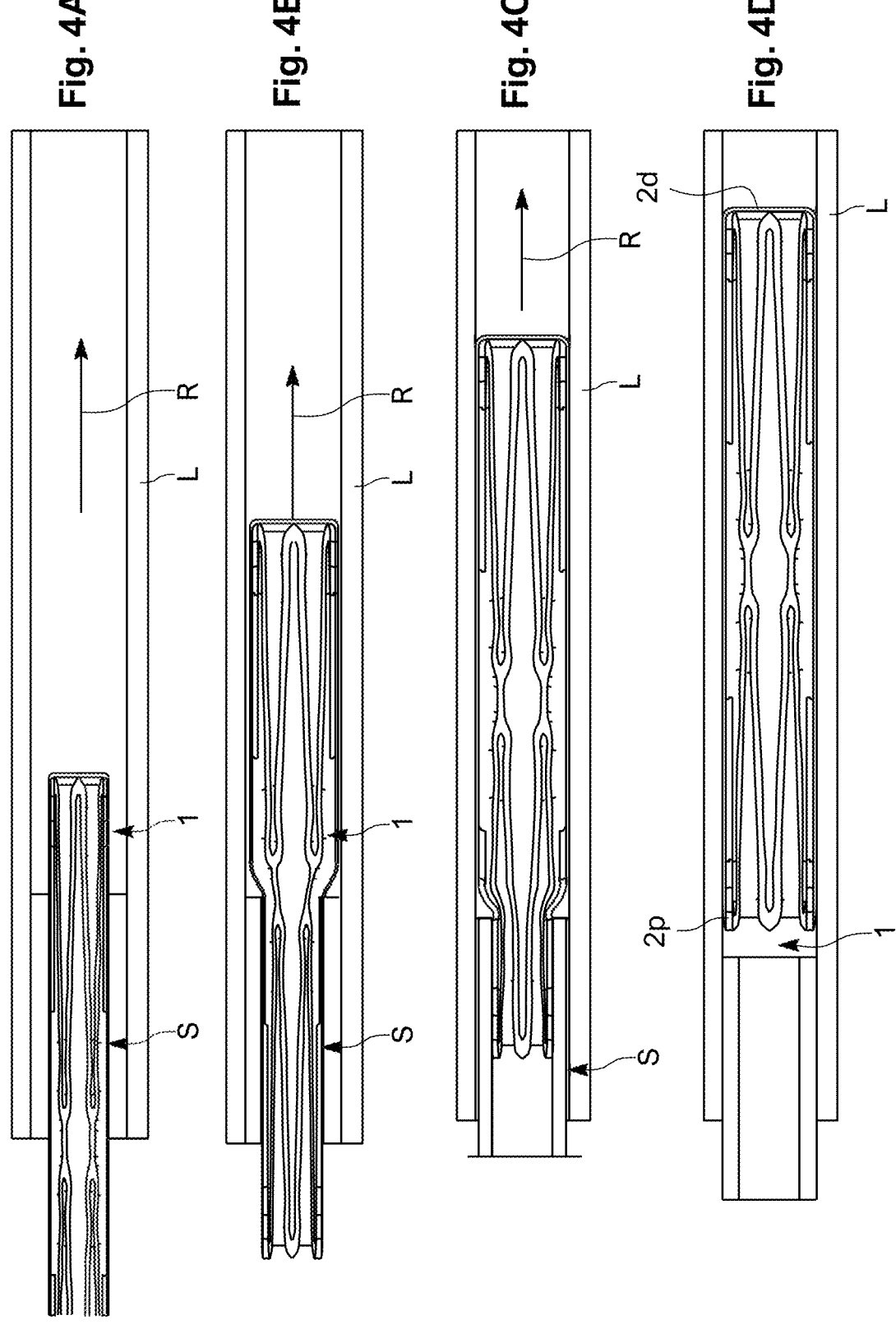

REVERSIBLE OCCLUSION DEVICE, SYSTEM AND METHOD

TECHNOLOGICAL FIELD

The present invention is in the field of body lumen occlusion, in particular, devices and methods for lumen occlusion and their re-opening.

BACKGROUND OF THE INVENTION

Contraception is a critical component of reproductive health, enabling individuals and couples to effectively control their fertility. While a variety of contraceptive methods are available, options specifically designed for male use are limited. Existing methods for male contraception predominantly include condoms, which are single-use and susceptible to failure, and vasectomy, which is highly effective but may be slightly intimidating for patients.

Alternative methods of male contraception have been explored, including chemical-based contraceptives and hormone-based therapies. However, these approaches face significant challenges. Chemical-based methods often result in severe side effects, making them unsuitable for widespread use. Hormonal contraceptives, while promising, suffer from low user acceptance due to potential side effects such as mood swings, weight gain, and alterations in libido, as well as the stigma associated with their use.

Another method is directed to plugging the vas deferens, thereby preventing sperm from flowing across the seminal vesicle. Existing approaches include injectable hydrogels, polymer plugs, and external clamps. Procedures are normally performed under local anesthetic, wherein the occlusion device is introduced using a syringe, directly pushing the plug into the lumen it is configured for blocking.

Acknowledgement of the above references herein is not to be inferred as meaning that these are in any way relevant to the patentability of the presently disclosed subject matter.

GENERAL DESCRIPTION

In accordance with one aspect of the subject matter of the present application, there is provided a reversible occlusion device configured for being introduced inside a lumen to selectively occlude it, said reversible occlusion device comprising a docking unit configured for being docked in the lumen and having, when positioned in the lumen, an upstream end associated with an upstream portion of the lumen, and a downstream end associated with a downstream portion of the lumen, and an inner volume extending between a first opening at said upstream end, and a second opening at said downstream end, said reversible occlusion device further comprising at least one restricting element configured for transitioning, at least once, between a first, closed position, in which it obstructs passage of material across said cavity between said first opening and said second opening, and a second, open position, in which it allows passage of material across said cavity between said first opening and said second opening, wherein in both said closed position and said open position, a peripheral portion of said restricting element is in contact with said docking unit.

It should be noted that the term 'reversible' used herein should be understood to refer to a reversibility of a process, rather than reversibility of direction. More particularly, it should be understood as referring to the ability to switch between two or more states.

The docking unit may be of a tubular shape, wherein said inner volume is the volume defined by the geometry of the tubular docking unit, and the first and second openings are defined by the open ends of the tubular docking unit. It should be understood that the term 'tubular docking unit' is used herein to refer to any 3D geometry extending along a longitudinal axis, and having a hollow or semi-hollow cross-section. For example, a tubular docking unit may refer to a structure having a polygonal cross-section such as a hollow prism, and may also refer to a hollow docking unit having a discontinuous cross-section, for example a perforated tube or a tubular mesh-structure.

In accordance with one example, the docking unit may be made of continuous material extending between the first end and the second end of the docking unit. Under this configuration, the docking unit may be formed with an external surface configured for interaction with said lumen, and an internal surface defining at least a portion of said cavity and facing it. Thus, when the docking unit is inserted into the lumen, a wall of the docking unit is disposed between the lumen and the cavity.

In accordance with a specific example, the docking unit may comprise a scaffold having a mesh structure, and being either covered or integrated with a sheath, forming a continuous surface along the docking unit, to come into contact with the lumen. Alternatively, the sheath may not fully cover the scaffold, whereby, when the reversible occlusion device is introduced into the lumen, the lumen is exposed to the cavity of the docking unit.

The docking unit may be configured for assuming at least:

a first, collapsed state, having a first nominal cross-section dimension;

a second, expanded state, having a second nominal cross-section dimension, greater than the first nominal cross-section dimension; and a plurality of intermediate states between said first, collapsed state and said second, expanded state, having a range of cross-section dimensions greater than said first nominal cross-section dimension and smaller than said second nominal cross-section dimension.

At least in the first, collapsed position, the reversible occlusion device is configured for being sized and shaped for being introduced into a delivery system including a delivery tube, the tube being configured for introducing the docking unit into a lumen. In operation, the tube may be introduced into the lumen and thereafter push the reversible occlusion device (or, in some cases, just the docking unit) into the lumen, in its first, collapsed state. Once the docking unit exits the delivery tube (which is smaller in diameter than the lumen), it is free to expand into its second, expanded state, pressing against a lumen wall. In this state, the reversible occlusion device is secured inside the lumen, and the restricting element prevents passage of material through the lumen.

In accordance with one design variation, the docking unit may be made of a flexible material, whereby the transition between the first, collapsed state and the second, expanded state, relies on the elastic properties of said flexible material. In accordance with another design variation, the scaffold may be in the form of a collapsible structure, whereby the transition between the first, collapsed state and the second, expanded state, relies on the mechanical structure of the scaffold. In accordance with a third design variation, the docking unit may combine both a flexible material and a mechanical structure in order to allow it to transition between the different states.

In accordance with a particular example, regardless of the manner in which the reversible occlusion device is configured for transitioning between the aforementioned states, the reversible occlusion device may comprise certain material memory capabilities, being biased into assuming its expanded position.

The reversible occlusion device may be used as birth contraceptive, in particular, as a male contraceptive. Specifically, the lumen into which the reversible occlusion device is introduced may be a body lumen, more particularly, a genital lumen, and even more particularly the Epididymis or the Seminal vesicle (vas deferens).

The restricting element may be configured to withstand an influx of fluid advancing through the lumen, and preventing this fluid from either entering, exiting or progressing through the docking unit, depending on the orientation of the reversible occlusion device and the position of the restricting element with respect to the docking unit. In accordance with one configuration, the docking unit may be introduced into the lumen such that the restricting element is located downstream of an open end of the cavity, whereby the restricting element is configured for preventing fluid that enters the cavity from exiting from an opposite end of the docking unit. In accordance with another configuration, the docking unit may be introduced into the lumen such that the restricting element is located upstream of an open end of the cavity, whereby the restricting element is configured for preventing fluid from even entering the cavity (and hence reaching an opposite end of the docking unit). In accordance with yet another example, the restricting element may be located at any point between the ends of the docking unit, thereby preventing fluid flow across at least a portion of the docking unit.

In accordance with one design embodiment, the restricting element may be in the form of a tearable membrane covering an opening of said at least one cavity, wherein said tearable membrane is at least:

a. sufficiently strong for obstructing passage of material across said opening; and b. sufficiently thin to allow tearing/cutting thereof in order to allow passage of material across said opening, when torn.

The tearable membrane may constitute part of the sheath which is either adhered or integrally formed with the scaffold, in a way that allows it to withstand an influx of fluid advancing through the lumen, and preventing this fluid from either entering or exiting the lumen, depending on the orientation of the reversible occlusion device. Alternatively, the tearable membrane may be adhered to the sheath as a separate component.

The tearable membrane may be made of a thin sheet of material, which may be configured for being torn by an external device. In addition, the tearable membrane may be configured for providing a hermetic seal between one segment of the lumen located downstream of the reversible occlusion device and another segment of the lumen located upstream of the reversible occlusion device. In particular, the tearable membrane may have a skirt portion extending over the sides of the scaffold, whereby, when introduced into the lumen, said skirt portion is configured for being positioned between a lumen wall and the docking unit.

In accordance with one example, the membrane may have a variable thickness, wherein a peripheral portion of the membrane, located closer to the tubular docking unit of the reversible occlusion device, has a first thickness t1, and wherein a central portion of the membrane, closer to the longitudinal axis of the reversible occlusion device, has a second thickness t2<t1. Thus, the membrane is configured for being more easily torn/punctured at a central portion thereof than at a peripheral portion thereof.

In accordance with one design variation, the central portion of the membrane may constitute at least 50% of the membrane area, more particularly, at least 60% of the membrane area, even more particularly, at least 70% of the membrane area, and even more particularly, at least 80% of the membrane area. In accordance with a specific example, the width t may be in the range of 40 μm-60 μm, more particularly, 35 μm-55 μm, and even more particularly 30 μm-50 μm, while the width T may be in the range of 60 μm-80 μm, more particularly 55 μm-75 μm, and even more particularly 50 μm-70 μm.

The docking unit may be configured for engaging with a perforation device, configured for creating a tear or a puncture in the tearable membrane, thereby opening the cavity and effectively reversing the lumen occlusion. The perforation device may be the same device used for introduction of the reversible occlusion device into the lumen. Alternatively, the perforation device may be a dedicated perforation device, as will be discussed in detail with regards to another aspect of the present application.

The docking unit may further comprise at least one auxiliary opening arrangement which is mechanically biased for applying axial pressure on the tearable membrane, said pressure being insufficient for tearing the membrane, at least when positioned within the lumen. The auxiliary opening arrangement may be configured, once a tear or a puncture is formed in the membrane (for example, by said perforation device), to assist in expanding the tear/puncture, pushing the membrane outward (towards a lumen wall) thereby facilitating exposure of the opening of the cavity. In such a way, the puncture is guaranteed to re-open the reversible occlusion device.

In accordance with one example, the auxiliary opening arrangement may be constituted by a part of the scaffold and be in the form of one or more arms extending radially into the cavity of the docking unit, and are outwardly biased. In operation, when a tear is formed in the membrane, its resistance is reduced, allowing the one or more arms to pivot about an axis transverse to the longitudinal axis of the docking unit, thereby applying axial pressure on the membrane and causing it to open. The auxiliary opening arrangement is thus configured for displacing the tearable membrane to the periphery of the opening, so as not to obstruct it.

In accordance with a particular example, the arms may be pre-formed as part of the scaffold, extending axially. During the manufacturing process, the arms may be bent or deformed to become radially facing, before the tearable membrane is integrated with the scaffold of the reversible occlusion device. Owing to certain flexibility in the structure of the arms, they apply pressure on the membrane, attempting to return to their original axially directed orientation, which can only take place once the membrane is cut.

In accordance with another design embodiment, the restricting element may comprise at least one resilient portion/segment, and formed with at least one aperture configured for being normally open. The reversible occlusion device may further comprise a pressure arrangement configured for at least partially displacing within said docking unit, and configured for transposing between:

i. normally assuming a first, pressure position in which it applies pressure on said resilient material, resulting in deformation of the resilient material, closing off said aperture and forming a continuous cover obstructing said first or said second opening, thereby bringing the restricting element to its first, closed state; and ii. assuming a second, release position, in which it applies less pressure on said resilient material, thereby allowing the aperture of said restricting element to become opened, whereby said restricting element transitions to its second, open position.

According to one example, the restricting element may be in the form of a torus or an annular member, allowing fluid communication between an opening of the reversible occlusion device and a hole of the torus/annular member. When the pressure arrangement displaces within the reversible occlusion device to apply pressure to the restricting element, the resilient nature of the latter may cause it to deform and expand, thereby closing off said hole, effectively blocking the opening of the reversible occlusion device. When the pressure arrangement is displaced in an opposite direction, the pressure on the restricting element is relieved, allowing it to return to its natural geometry wherein the hole is opened.

In accordance with another example, the restricting element may have a tapering portion terminating at said at least one aperture, the tapering portion being configured for being opened outwards, and bearing against said docking unit. The docking unit may be formed with a closing edge, wherein, when said restricting element is linearly displaced towards said restricting edge, the tapering portion bears against the restricting edge, causing the aperture to close. Conversely, linear displacement of the restricting element away from the restricting edge may cause the tapering portion to open up the aperture.

In accordance with yet another example, the restricting element may be in the form of a removable plug configured for assuming at least a first position, in which it fills the cavity of the docking unit, thereby yielding the first, closed position of the reversible occlusion device, and at least a second position in which it is removed from the docking unit, thereby yielding the second, open position of the reversible occlusion device. In this example, the docking unit may be fixed to the lumen and function as a docking station for the removable plug.

In accordance with still another aspect of the subject matter of the present application, there is provided a reversing apparatus for the reversible occlusion device of the previous aspect of the present application, said reversing apparatus comprising at least one working end configured for engaging, directly or indirectly, with said restricting element for transitioning it at least from its first, closed position, to its second, open position.

In accordance with one example, when the restricting element is a tearable membrane, the reversing apparatus may be in the form of a perforation device comprising a housing and at least one spike formed with a pointed tip configured for puncturing the membrane, said spike being configured for displacing within the housing between at least a first, retracted position in which said tip is spaced $A_1$ distance from a distal end of the housing, and a second, extended position, in which said tip is spaced a distance $A_2$ from the distal end of the housing, wherein $A_2 < A_1$.

The perforation device may further comprise at least one cutting element laterally extending from said housing, said cutting element being configured, once the membrane is punctured by the tip of the spike, to cut at least a portion of the tearable membrane still attached to the scaffold. Said at least one cutting element may constitute part of a cutting and removal module, also configured for removing at least the cut portion of the membrane, cut by the cutting element.

In accordance with a particular example, the cutting and removal module may comprise one or more struts protruding from the housing, at least in the second, extended position of the spike, wherein at least one of said structs comprises said cutting element, and wherein the circumferential diameter of the struts corresponds in size and shape to the size of the cross-section of the cavity of the docking unit. The cutting element may be oriented in a direction tangent to the circumference of the struts, being configured for cutting the tearable membrane when the perforation device is rotated about its axis.

In operation, the perforation device may be used as follows:

a. introducing of the perforation device into the lumen. At this stage, the spike may be in its retracted position, the tip of the spike being prevented from damaging the lumen or any surrounding tissue;

b. bringing a distal end of the housing in sufficient proximity to the tearable membrane;

c. transitioning the spike into its second, extended position, thereby puncturing the tearable membrane with the tip of the spike;

d. advancing the perforation device towards the membrane such that the struts of the cutting and removal module are aligned with a peripheral portion of the membrane;

e. rotating the perforation device about an axis thereof such that the cutting element cuts at least a portion of the center of the membrane; and f. pulling the perforation device away, whereby the struts pull out at least a portion of the membrane that was cut.

In accordance with a further aspect of the subject matter of the present application, there is provided a reversible occlusion system comprising a reversible occlusion device according to the first aspect of the present application, and a reversing apparatus according to the second aspect of the present application.

In accordance with still another aspect of the subject matter of the present application, there is provided a method for reopening a reversible occlusion device according to a previous aspect of the present application, the method comprising the steps of:

a. providing a lumen accommodating therein a reversible occlusion device according to the previous aspect of the present application;

b. introducing a dedicated device into said lumen; and c. using said dedicated device in order to transition said restricting element from said first, closed position to said second, open position.

Depending on the form of the restricting element, step (c) may be performed as any one or more of the following:

i. tearing said restricting element;

ii directly or indirectly displacing said restricting element along said docking unit; and iii. removing the restricting element from the docking unit.

In accordance with a specific variation, the method may include an additional step of introducing an additional reversible occlusion device into the lumen, to be placed in tandem with the opened reversible occlusion device.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2A is a schematic longitudinal cross-section of the reversible occlusion device shown in FIGS. 1A and 1B;

FIG. 2B is a schematic enlarged view of a top portion of the cross-section shown in FIG. 2A;

FIG. 2C is a schematic illustration of the membrane of the reversible occlusion device as shown in FIG. 2B;

FIGS. 4A to 4D are schematic longitudinal cross-sections of the reversible occlusion device shown in FIGS. 1A and 1B, during different stages of insertion of the reversible occlusion device into a lumen;

Figures 1A, 1B:
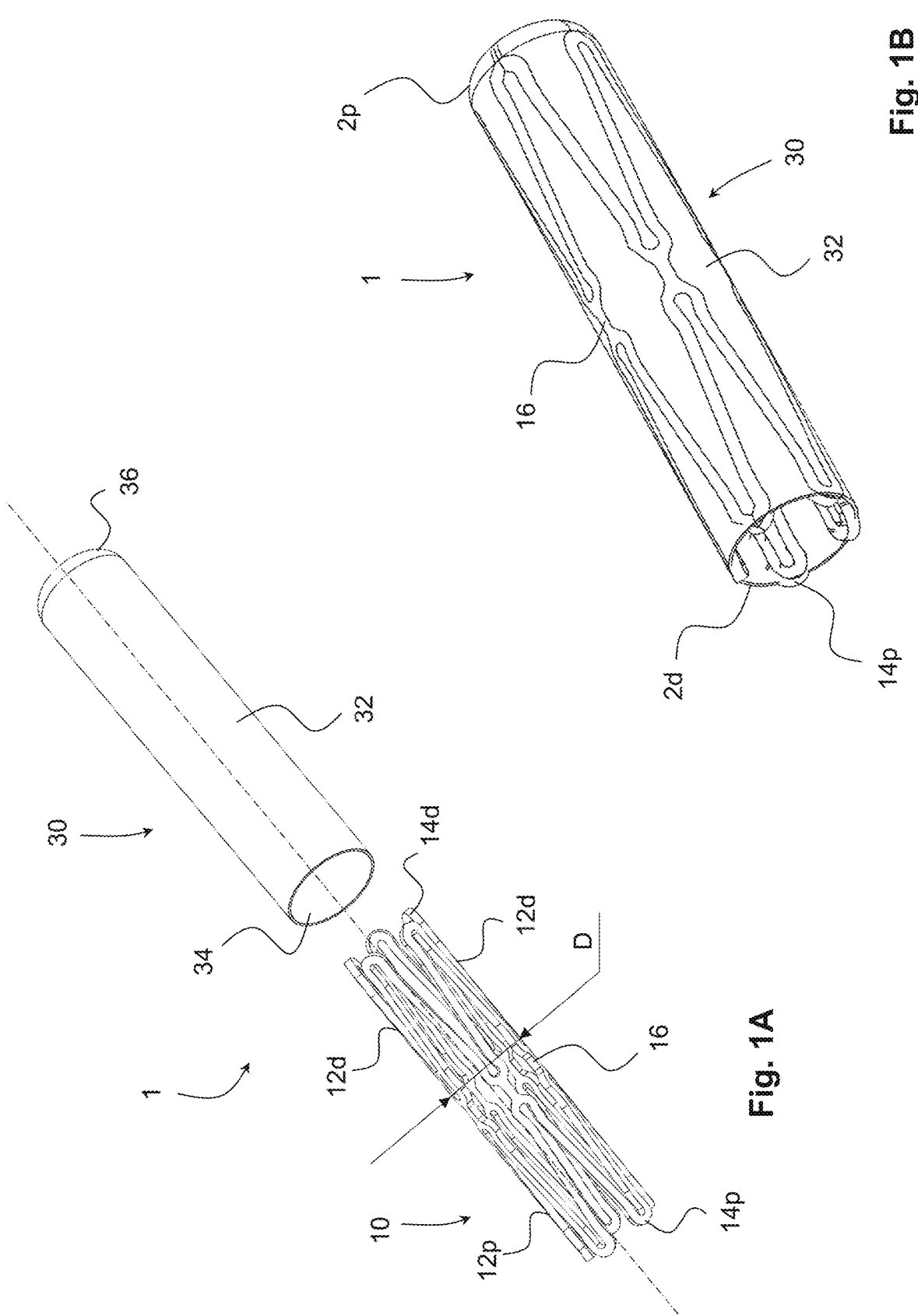
FIG. 1A is a schematic exploded isometric view of a reversible occlusion device according to the present application.
FIG. 1B is a schematic isometric view of the reversible occlusion device shown in FIG. 1A.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF EMBODIMENTS

Attention is first drawn to FIGS. 1A and 1B, in which a reversible occlusion device is shown, generally designated 1, and comprising a scaffold 10 integrated with a sheath 30. The reversible occlusion device 1 is configured for being inserted into a lumen (shown, for example, in FIGS. 4A-4D), in order to block passage of substance/content/material from an upstream side of the lumen to a downstream side of the lumen.

The scaffold 10 has a body extending along a longitudinal axis, between a proximal end and a distal end. The scaffold 10 is made of a set of struts having a proximal portion 12*p*, and a distal portion 12*d*, each strut being formed with a rounded end portion 14*p*, 14*d* respectively. In the middle of the scaffold 10, each pair of struts 12*p* and 12*d* are connected by an intermediate connecting portion 16.

The sheath 30 is in the form of a cylinder 32 with an opening 34 at the proximal end, and a cover membrane 36 at the closed end, which forms part of the cylinder 32. The scaffold 10 is integrated with the sheath 30 during manufacturing, in such a way that it becomes embedded within the cylinder 32.

It should be noted here that the cylinder 32 together with the scaffold 10 constitute the docking unit, and the cover membrane 36, which, in this example, is part of the sheath 30, constitutes the restricting element.

It should also be noted that while the current example refers to a docking unit which is restricted only at one end thereof, other configurations may be conceived in which both ends of the docking unit are restricted by a restricting member.

With additional reference being drawn to FIGS. 2A to 2C, the membrane 36 extends over the distal end of the scaffold 10, such that it blocks passage of any material from one side of the reversible occlusion device 1 to the other along the longitudinal direction. The membrane 36 is formed with a peripheral portion 36*p*, having a thickness T, and a central portion 36*c*, having a smaller thickness t<T. The membrane extends across the distal opening with a certain amount of tension such that even the smaller thickness t is sufficient for resisting flow of material without tearing. On the other hand, the smaller thickness t of the central portion 36*c* facilitates easier dedicated puncturing of the membrane 36, by a perforation device 50 (shown FIGS. 5A to 5D). The membrane 36 may be made of a resilient material such as silicone, thin rubber etc., which meets the criteria defined above.

Figures 3A, 3B, 3C:
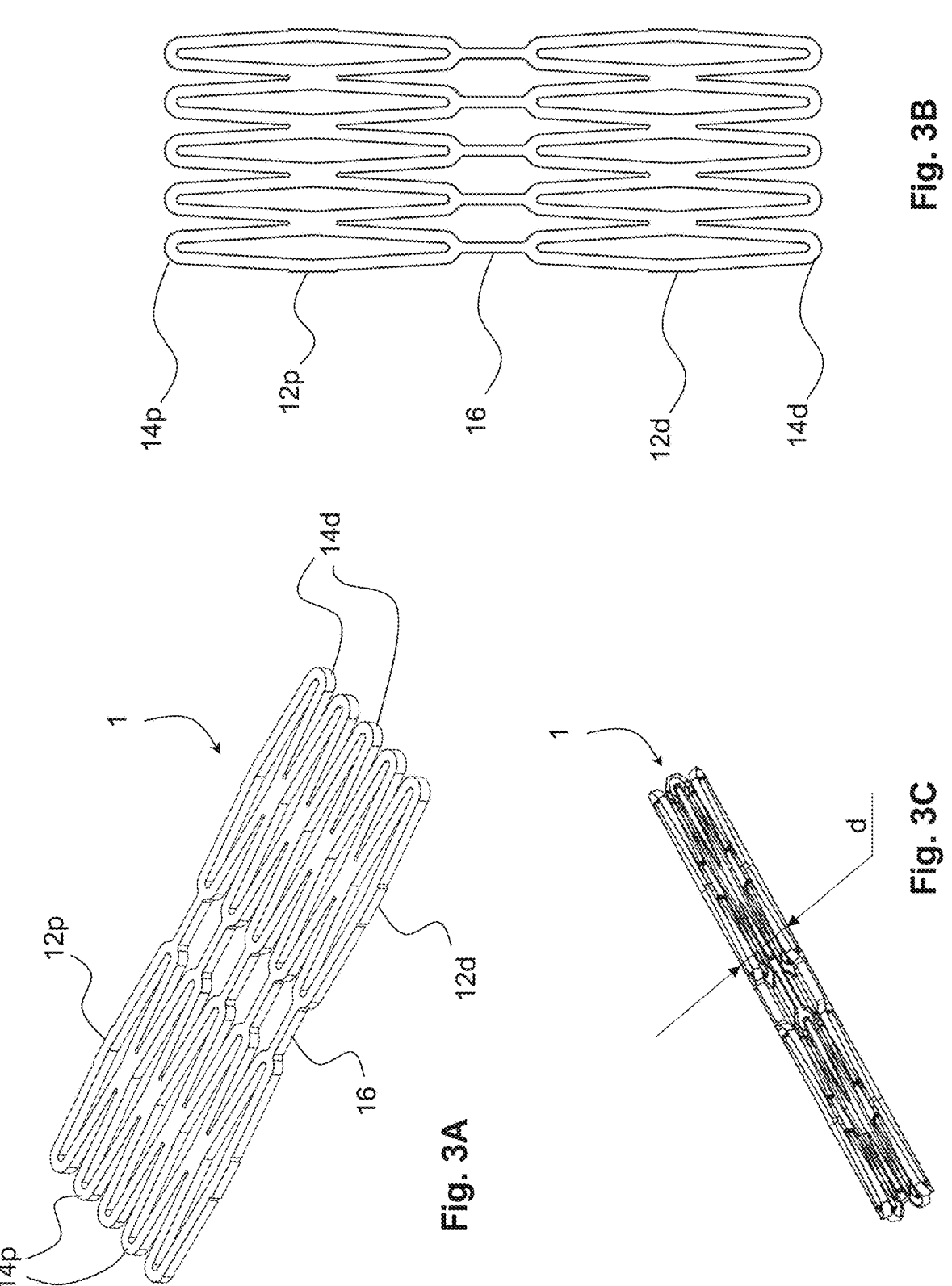
FIG. 3A is a schematic isometric view of a flat sheet to be rolled into a component of the reversible occlusion device shown in FIGS. 1A and 1B.
FIG. 3B is a schematic front view of the flat sheet shown in FIG. 3A.
FIG. 3C is a schematic isometric view of a component of the reversible occlusion device shown in FIGS. 1A and 1B, shown in its contracted state.

Turning now to FIGS. 3A to 3C, the scaffold 10 is manufactured out of a flat 2-D mesh cut to be formed with the struts 12*p*, 12*d*, rounded end portions 14*p*, 14*d*, and connecting portion 16. Once manufactured, it can be rolled along its length dimension to form the scaffold 10. The design of the scaffold 10 allows the scaffold to transition from a naturally expanded position (shown FIGS. 1A-1B), in which it has a nominal cross-sectional diameter D, to a collapsed state as shown in FIG. 4C, in which it has a much smaller nominal cross-sectional diameter d<<D. The reversible occlusion device 1 is configured for assuming its naturally expanded position when positioned within the lumen, and to assume its collapsed state when inserted into a leading tube in order to be introduced into the lumen.

Turning now to FIGS. 4A to 4D, the steps of introducing the reversible occlusion device 1 into the lumen are shown. In FIG. 4A, the reversible occlusion device 1 is received, in its collapsed state, within a leading tube S. The tube S is shown being introduced into the lumen L via an incision (shown FIGS. 11A-11B), until it is situated at the proper location for positioning of the reversible occlusion device 1. In this state, the leading tube S serves as a working channel for the introduction of the reversible occlusion device 1. In the position shown in FIG. 4A, the reversible occlusion device 1 has already been slightly pushed forward by a pushing mechanism (not shown), such that a tip thereof protrudes from a distal end of the leading tube S. In this position, the portion of the reversible occlusion device 1 is still in a collapsed state, as most of it is still received within the tube S.

Thereafter, as shown in FIG. 4B, the reversible occlusion device 1 is further pushed from the leading tube S in the direction of arrow R, where the portion thereof that protrudes from the leading tube S begins to expand in order to occlude the lumen.

In FIG. 4C, the reversible occlusion device 1 is pushed even further into the lumen L, while the leading tube slightly retreats in a direction opposite the insertion direction. Finally, as shown in FIG. 4D, the reversible occlusion device 1 is completely outside the leading tube S, and is free to expand to its expanded position, in which the sides of the reversible occlusion device 1 abut the walls of the lumen L, effectively blocking passage of material from an upstream direction to a downstream direction. Specifically, the sheath cylinder 32 pushes against the wall of the lumen L, preventing passage of material between the sheath 32 and the lumen L, and the membrane 36 at the distal end 2d prevents passage of material through the reversible occlusion device 1. In the position shown in FIG. 4D, the procedure for introducing the reversible occlusion device 1 into the lumen L is completed, and the lumen L is effectively closed.

Figures 5A, 5B:
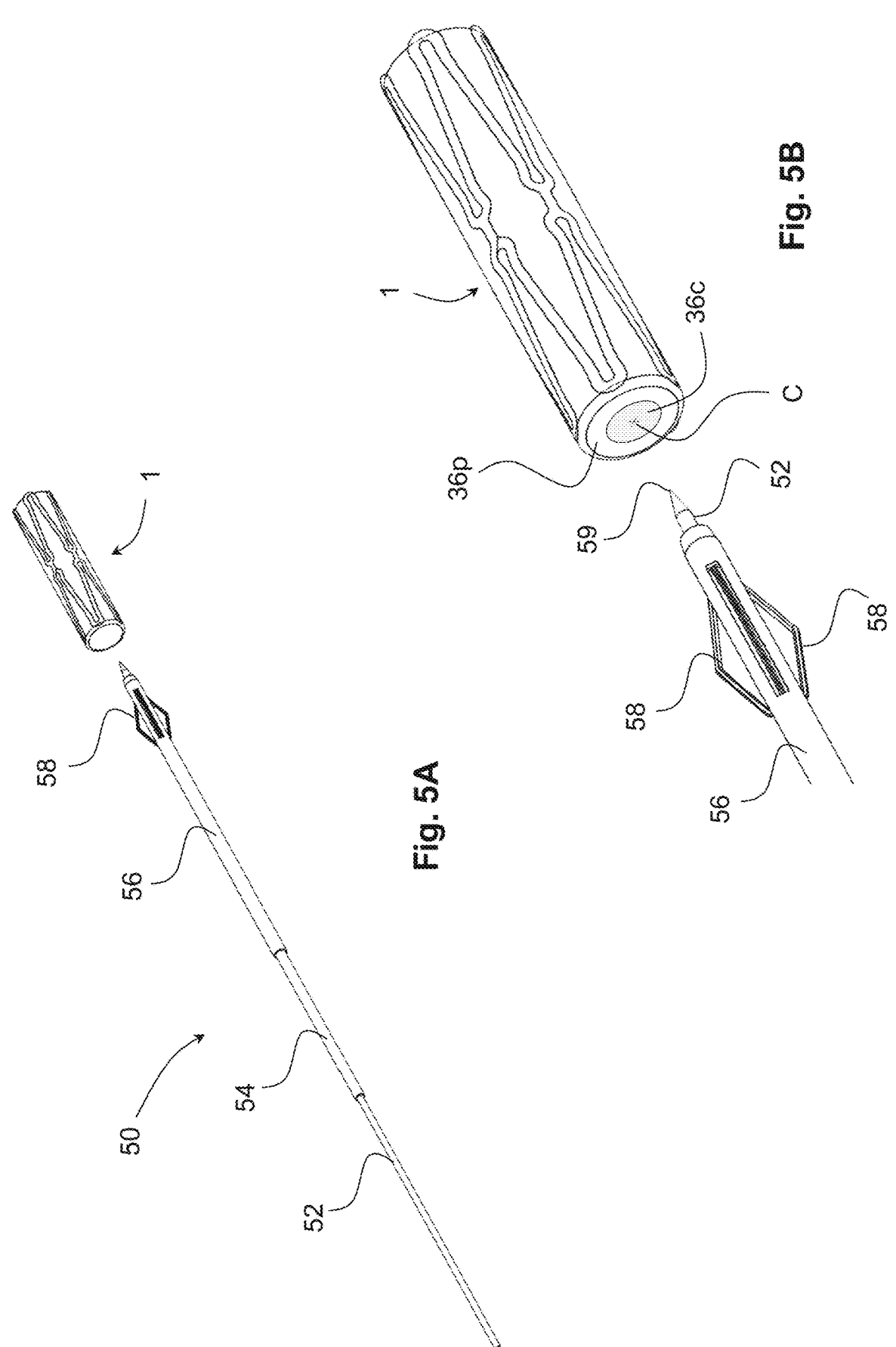
FIG. 5A is a schematic isometric view of the perforation device configured for opening the reversible occlusion device shown in FIGS. 1A and 1B, when approaching the reversible occlusion device.
FIG. 5B is a schematic enlarged view of a tip of the perforation device in proximity to the reversible occlusion device as shown in FIG. 5A.
Figure 5C:
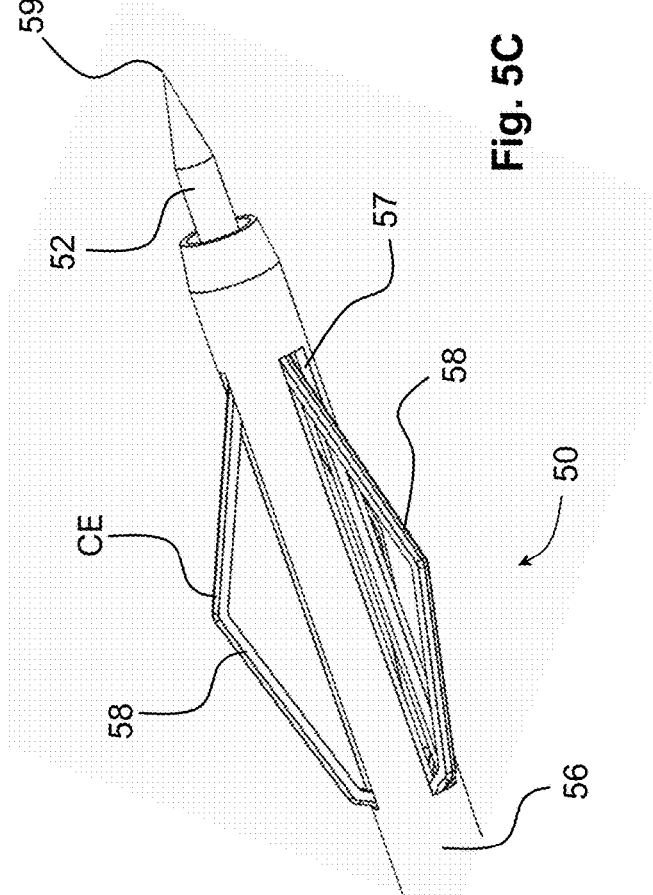
FIG. 5C is a schematic enlarged view of a tip of the perforation device shown in FIG. 5B.
Figure 5D:
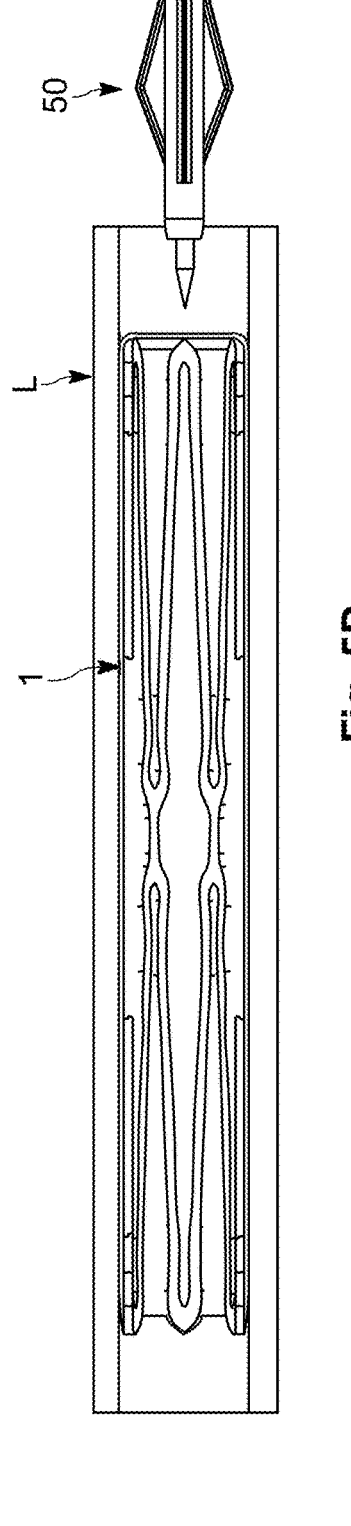
FIG. 5D is a schematic lateral view of the perforation device of FIGS. 5A to 5C, when entering a lumen in which the reversible occlusion device is located.

Turning now to FIGS. 5A to 5C, in the event that the procedure needs to be reversed, i.e. allowing passage of material through the lumen L across the reversible occlusion device 1, a dedicated perforation device 50 may be introduced into the lumen L, to pierce the membrane 36. The perforation device 50 comprises a puncturing needle 52 slidingly received within a set of tubes 54, 56, the needle 52 having a sharp tip 59 configured for being aligned with a center C of the central portion 36*c* of the membrane 36. With specific reference to FIG. 5C, the perforation device 50 may be introduced into the lumen L when the needle 52 is retracted, the tip 59 being received within the tube 56. When the perforation device 50 reaches the reversible occlusion device 1, and is properly aligned, the needle 52 may be pushed towards the membrane 36, exposing the tip 59, allowing it to puncture the membrane 36.

Furthermore, the tube 54 is formed with foldable struts 58 configured for protruding out of the tube 56 via dedicated slots 57. These struts 58 may be formed with a cutting edge CE, configured for cutting away at least a portion of the membrane 36. Specifically, when the membrane has been punctured, the perforation device 50 can be rotated about its central axis, whereby the cutting edges CE of the struts 58 scrape against a periphery of the rim of the reversible occlusion device 1, thereby ensuring the central portion 36*c* of the membrane 36 being properly removed after puncturing.

Thus, the steps of puncturing may be as follows:
1. introducing the perforation device 50, with the tip 59 of the needle 52 covered;
2. Aligning the perforation device within the lumen L;
3. Telescopically axially sliding the tube 54 within the tube 56, causing the struts 58 to protrude from slots 57, and abutting the wall of the lumen L; and
4. Axially pushing the needle 52 forward such that the tip 59 punctures the center C of the membrane 36; and
5. Rotating the perforation device 50 such that the cutting edges CE cut the membrane along the peripheral portion thereof.

As a result of the tension of the membrane 36, puncturing the membrane causes it to rupture (similarly to a balloon), causing the distal end 2d of the reversible occlusion device 1 to become fully opened, thereby allowing passage of material within the lumen L across the reversible occlusion device 1. However, it should be noted, that the cutting operation performed by the rotation of the perforation device 50, removes the central portion 36*c* of the membrane 36, while the peripheral portion 36*p* thereof remains attached to the sheath 30 of the docking unit.

In this manner, the functionality of the reversible occlusion device 1 may be completely reversible.

Figures 5E, 5F, 5G:
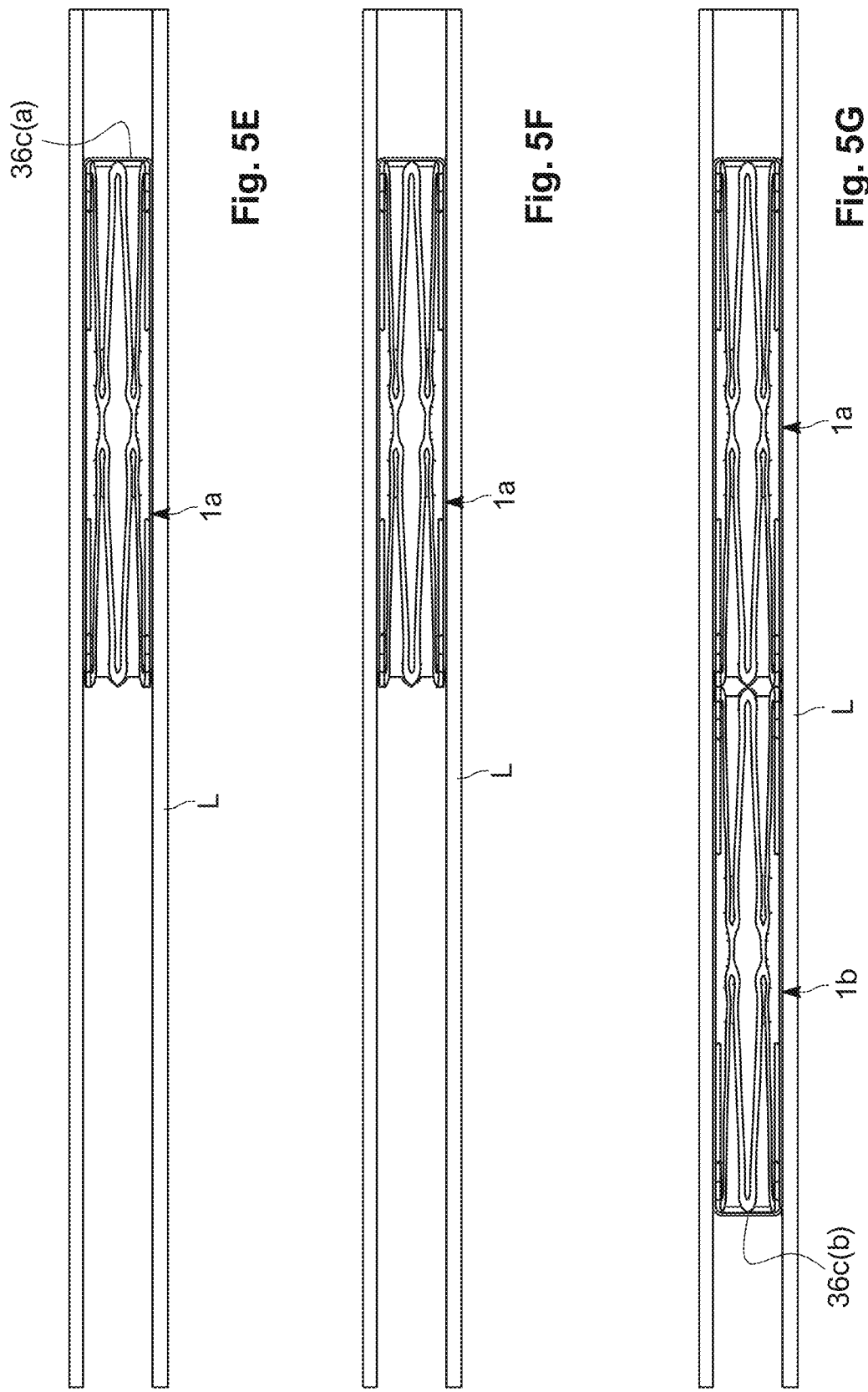
FIG. 5E is a schematic longitudinal cross-sectional view of the reversible occlusion device shown in FIGS. 4A to 4D, before being perforated.
FIG. 5F is a schematic longitudinal cross-sectional view of the reversible occlusion device shown in FIGS. 4A to 4D, after being perforated.
FIG. 5G is a schematic longitudinal cross-sectional view of the reversible occlusion device shown in FIGS. 4A to 4D, including an additional reversible occlusion device introduced in tandem.

Additional attention is drawn to FIGS. 5E to 5G, in which a specific method is shown, involving the use of two or more reversible occlusion devices 1*a* and 1*b*. In the state shown in FIG. 5E, the reversible occlusion device 1*a* is safely situated within the lumen L, occluding it and preventing passage of fluid from one end of the device 1 to the other.

In the state shown in FIG. 5F, the membrane 36*a* of the reversible occlusion device 1*a* has been perforated (in a manner similar to that shown in FIGS. 5A to 5D), and the central portion 36*c* (a) thereof has been completely removed in order to reverse the occlusion. In this state, fluid can flow freely through the now opened reversible occlusion device 1*a*, as if the procedure never took place.

In the state shown in FIG. 5G, if it is desired to again occlude the lumen L, a method is shown not involving the repair or re-introduction of a membrane into the reversible occlusion device 1*a*. Instead, an additional reversible occlusion device 1*b* is introduced into the lumen L, in tandem, this reversible occlusion device having a membrane 36*b*, configured for serving the same function as the previously torn membrane 36*a*. It should be noted that the reversible occlusion device 1*b* is introduced into the lumen L with the membrane 36*b* thereof facing away from the reversible occlusion device 1*a*, thereby facilitating easier access to the membrane 36*b*, if perforation thereof is required in the future.

Figures 6A, 6B, 6C, 6D:
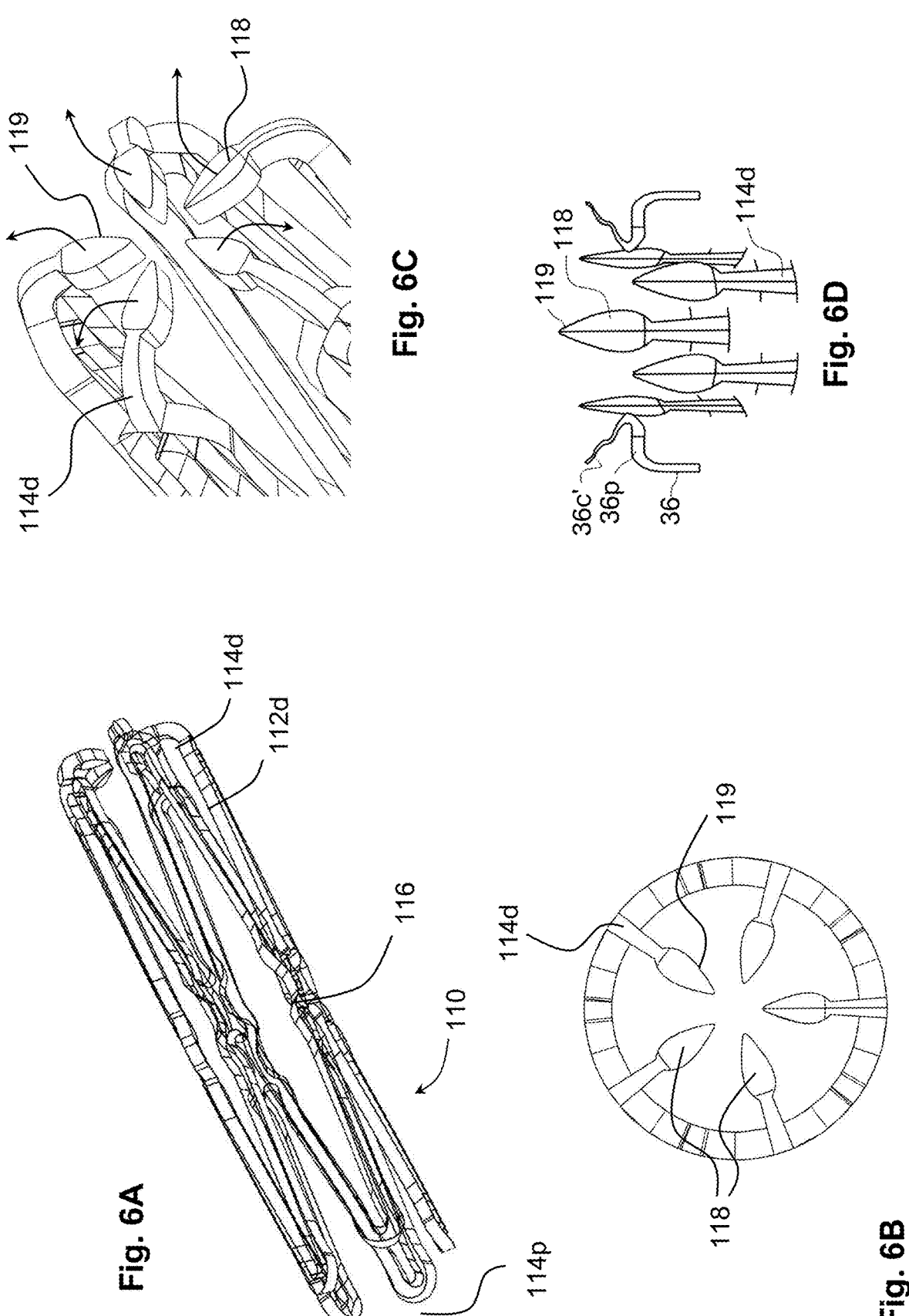
FIGS. 6A and 6B are schematic isometric and top views of another embodiment of a reversible occlusion device component according to the present application.
FIG. 6C is a schematic enlarged view of a distal portion of the component shown in FIGS. 6A and 6B.
FIG. 6D is a schematic illustration of the component shown in FIGS. 6A to 6C, after puncture of a membrane.

Attention is now drawn to FIGS. 6A to 6D, in which another design of the scaffold is shown, generally designated 110, and differing from the previous reversible occlusion device by the design of the distal end thereof. Specifically, the proximal end is formed with the same structs 112*p* and rounded end portions 114*p*, but the distal end is formed with specially designed end portions 114*d*, each formed with a spear-like opening tip 118, having an edge 119. The rounded end portions 114*d* are configured for extending axially (as shown in FIG. 6D), but during manufacture, they are bent inwards, such that the tips 118 point radially towards the central axis of the scaffold 110. When the sheath 30 is integrated over the scaffold 110, the membrane 36 extends over the bent tips 118, preventing them from returning to their axially extended position. Thus, this bending causes the tips 118 to exert axial pressure on the membrane 36.

With specific reference being made to FIG. 6D, when the membrane 36 is punctured, its resistance to the bending of the tips 118 is reduced, and the latter can assume their axially extended state. This extension of the tips 118 allows pushing the remains of the torn membrane 36 outwardly, clearing the central cavity 34 of the reversible occlusion device 1 for passage of material. The right angle at the tip 118, forming the edge 119, further facilitates tearing any remaining pieces of the membrane after it has been punctured.

Figures 7A, 7B:
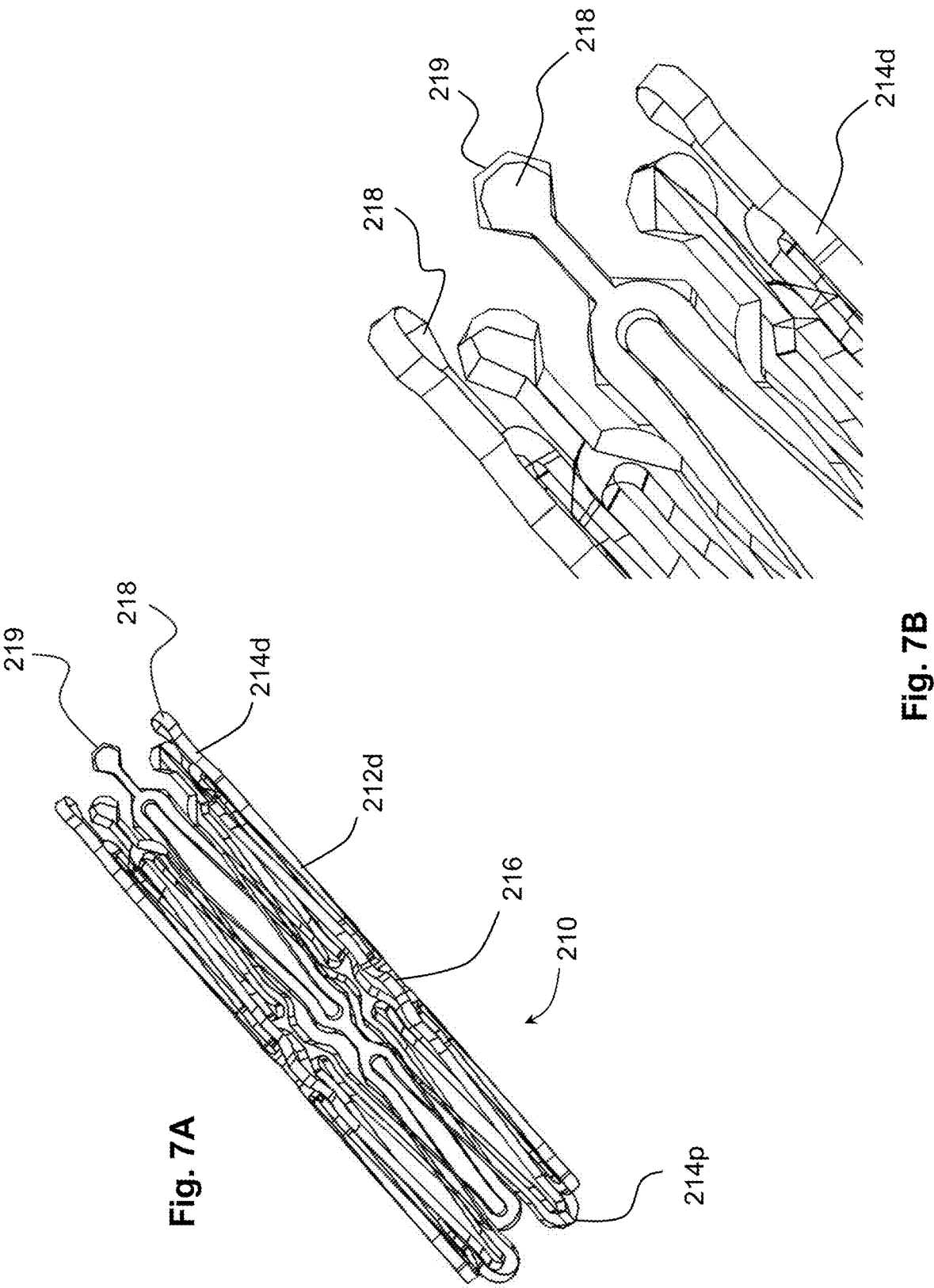
FIG. 7A is a schematic isometric view of another embodiment of a reversible occlusion device component according to the present application.
FIG. 7B is a schematic enlarged view of a distal portion of the component shown in FIG. 7A.

Turning now to FIGS. 7A and 7B, another example of a scaffold is shown, generally designated 210, and comprising rounded tips 218, as opposed to a spear-like shape. The scaffold 210 is shown in FIGS. 7A and 7B in its axially extended position (bent position not shown). The opening principle is the same (bent end portion 214 extending axially once the membrane 36 is torn). However, in this specific example, owing to the rounded geometry of the tips 218, there is a reduced risk of accidental rupture of the membrane 36 by the tips 218 themselves (instead of by the perforation device 50).

Figures 8A, 8B:
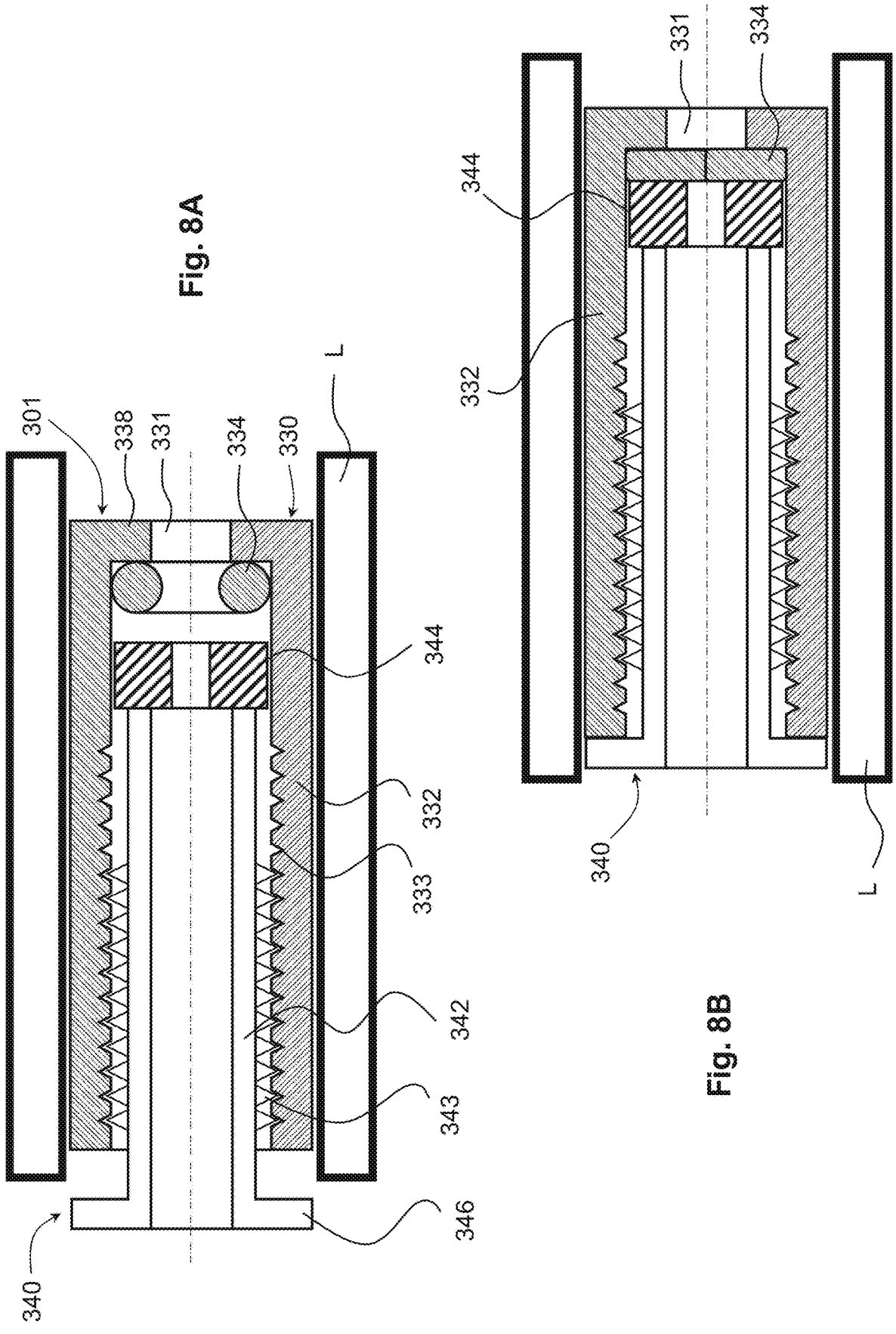
FIG. 8A is a schematic longitudinal cross-sectional view of a reversible occlusion device located within a lumen according to another example of the present application, shown in its closed position.
FIG. 8B is a schematic longitudinal cross-sectional view of the reversible occlusion device shown in FIG. 8A, shown in its open position.

Attentions is now drawn to FIGS. 8A and 8B, in which another configuration of the reversible occlusion device is shown, generally designated 301, and comprising a housing 330, receiving therein a restricting element 334, and a plunger 340. The housing 330 is configured for being received within the lumen L, and is in the form of a cylinder, the external surface of which is configured for abutting the lumen walls. The housing 330 is further formed, at a distal end thereof, with an opening 331, the opening being sized and shaped to leave a skirt portion 338 extending radially from the external surface of the housing 330. The restricting element 334 is in the form of a resilient O-ring located at the distal end of the housing 330, and abutting against the skirt portion 338 from the inside.

In addition, an inner surface of the cylinder 332 is formed with an inner threaded portion 333. The plunger 340 comprises a main shaft 342, having an outer threaded portion 343, configured for interacting with the inner threaded portion 333 of the housing 330, facilitating controlled axial movement of the plunger 340 relative to the housing 330. The plunger 340 further comprises a press 344, configured for engaging the restricting element 334.

In the state shown in FIG. 8A, the plunger 340 is in a distal position, the press 344 being spaced from the restricting element 334, and the restricting element is in its natural, open position, allowing free flow of fluid through the opening, its central opening being aligned with the opening 331.

When the plunger 340 is axially displaced within the housing 330 via rotation thereof along the threaded portions, the press 344 applies pressure on the resilient restricting element 334, causing it to deform and close off the opening 331, as shown in FIG. 8B. In essence, this allows the reversible occlusion device 301 to be controlled to assume either an open or a closed state, thereby allowing selective multiple opening and closing cycles of the reversible occlusion device 1. Furthermore, compared to the previously described examples involving a membrane, in this example, the change between an open and a closed state can be performed multiple times.

Figures 9A, 9B:
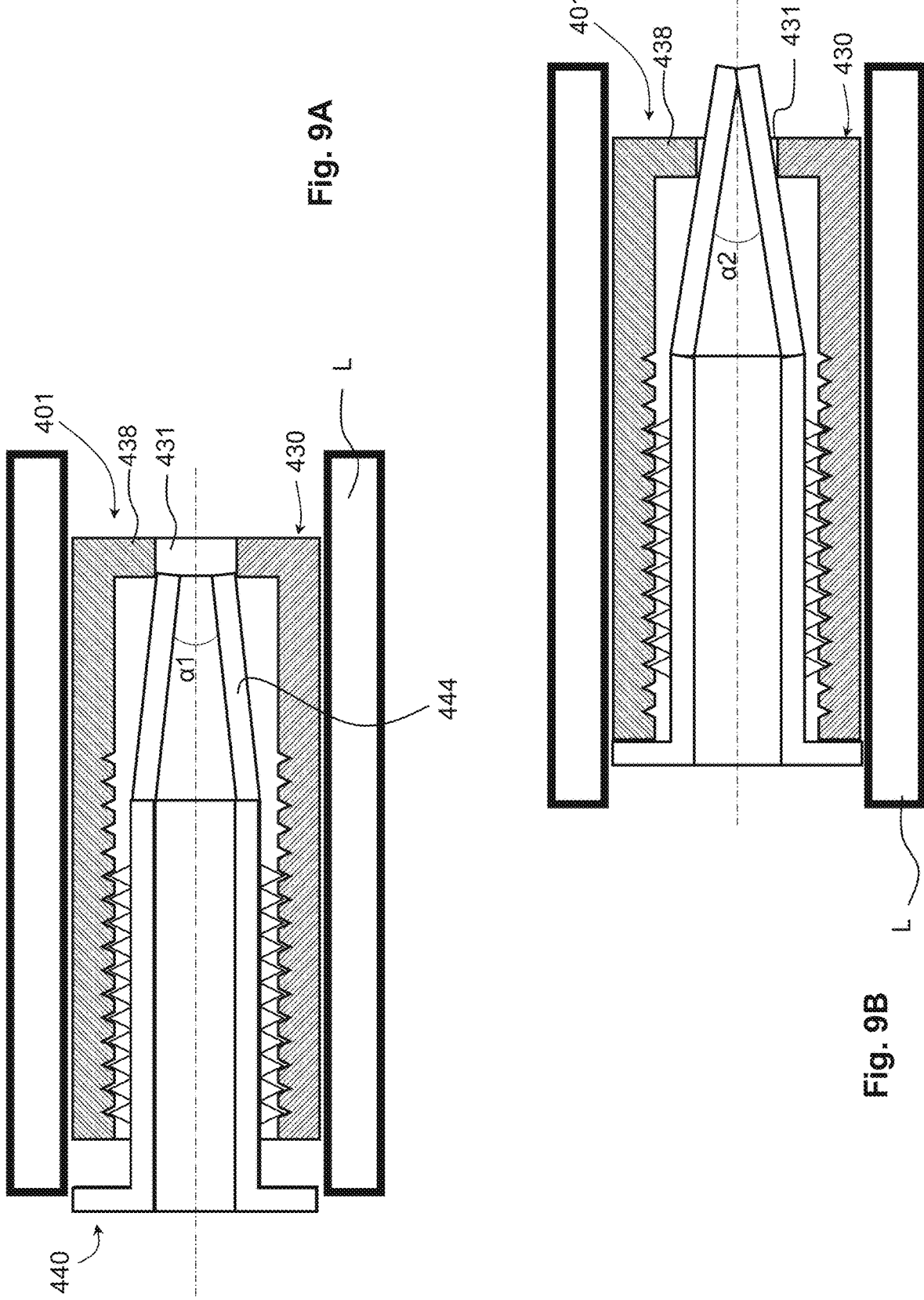
FIG. 9A is a schematic longitudinal cross-sectional view of a reversible occlusion device located within a lumen according to another example of the present application, shown in its closed position.
FIG. 9B is a schematic longitudinal cross-sectional view of the reversible occlusion device shown in FIG. 9A, shown in its open position.

Turning now to FIGS. 9A and 9B, another example of a multi-reopenable reversible occlusion device is shown, generally designated 401. In this example, the housing 430 is essentially similar to the housing 330 described in FIGS. 8A and 8B, but the design of the plunger 440 is different. Specifically, in this example, the restricting element 444 is constituted by an extension of the plunger 440, in the form of a conical portion or a duck-bill formation.

In the state shown in FIG. 9A, the plunger 440 is in a distal position, and the restricting element 444 is in its naturally open state. The geometry of the restricting element 444 is such that the angle $\alpha1$ is sufficient for maintaining the opening of the restricting element 444 in front of the opening 431, allowing fluid to pass through the reversible occlusion device 401.

When the plunger 440 is axially displaced within the housing 430 via rotation thereof along the threaded portions, the restricting element 444 is pushed into the opening 431, causing it to taper further, increasing the angle to $\alpha2$, effectively blocking the opening 431.

Similarly to the previous example, this reversible occlusion device 401 is also completely reversible and multi-usable, as the opening/closing is controlled by axial movement of the plunger 440.

Operation of the plungers 340 and 440 shown in FIGS. 8A to 9B may be performed by a dedicated device (not shown), comprising a working end configured for engaging with the head of the plunger 340/440, and an activation mechanism located outside the body, and configured for controlling the operation of the working end. Specifically, the working end of such a device may be introduced into the lumen L until it engages the head of the plunger 340/440, whereafter a user can operate the activation mechanism externally, thereby causing rotation of the work end and, by consequence, rotation of the plunger 340/440.

Figures 10A, 10B:
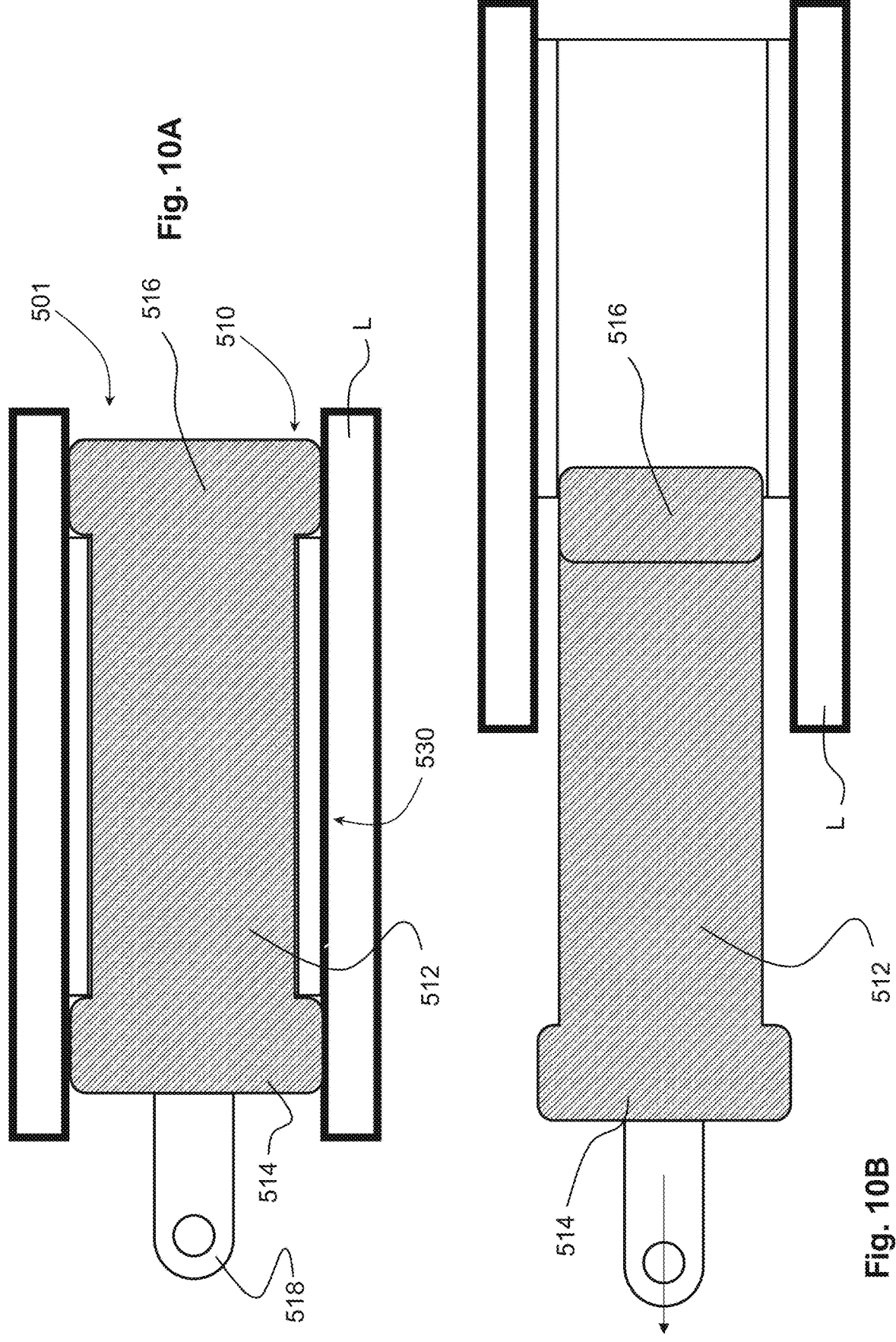
FIG. 10A is a schematic longitudinal cross-sectional view of a reversible occlusion device located within a lumen according to another example of the present application, shown in its closed position.
FIG. 10B is a schematic longitudinal cross-sectional view of the reversible occlusion device shown in FIG. 10A, shown in its open position.

Attention is now turned to FIGS. 10A and 10B, in which yet another example of a reversible occlusion device is shown, generally designated 501, and comprising a cylindrical housing 530, and a plug 510, having a scaffold 512, formed with a proximal end portion 514, and a distal end portion 516. The arrangement is such that the plug 510 is made of a flexible material, e.g. silicone, and the scaffold 512 is sized and shaped for being received within the housing 530. However, each of the proximal portion 514 and the distal portion 516 have a larger diameter than the housing 530, such that the plug 510 cannot spontaneously be removed from the housing 530. The plug 501 is further formed with an extension 518 configured for being grasped in order to pull on the plug 501.

In the state shown in FIG. 10A, the plug 510 is received within the housing 530, fully blocking any passage of fluid/material from one end of the reversible occlusion device 501 to the other. When it is desired to change the state of the reversible occlusion device 501, reversing the blocking function, a device may be introduced into the lumen L to grasp the extension 518, thereby pulling the plug 501 out of the housing 530, as shown in FIG. 10B. During this process, the distal portion 516 deforms and compresses, allowing it to pass through the housing 530. The plug 510 can thus be removed from the housing 530, clearing the way for fluid flow. When it is desired to again reverse the state of the reversible occlusion device 501, a new plug 510 may be re-introduced into the housing 530, in a manner opposite that shown in FIG. 10B, thereby closing off passage of fluid across the reversible occlusion device 501. As in previous examples, this design also provided a completely reversible and multi-usable reversible occlusion device.

Figure 12:
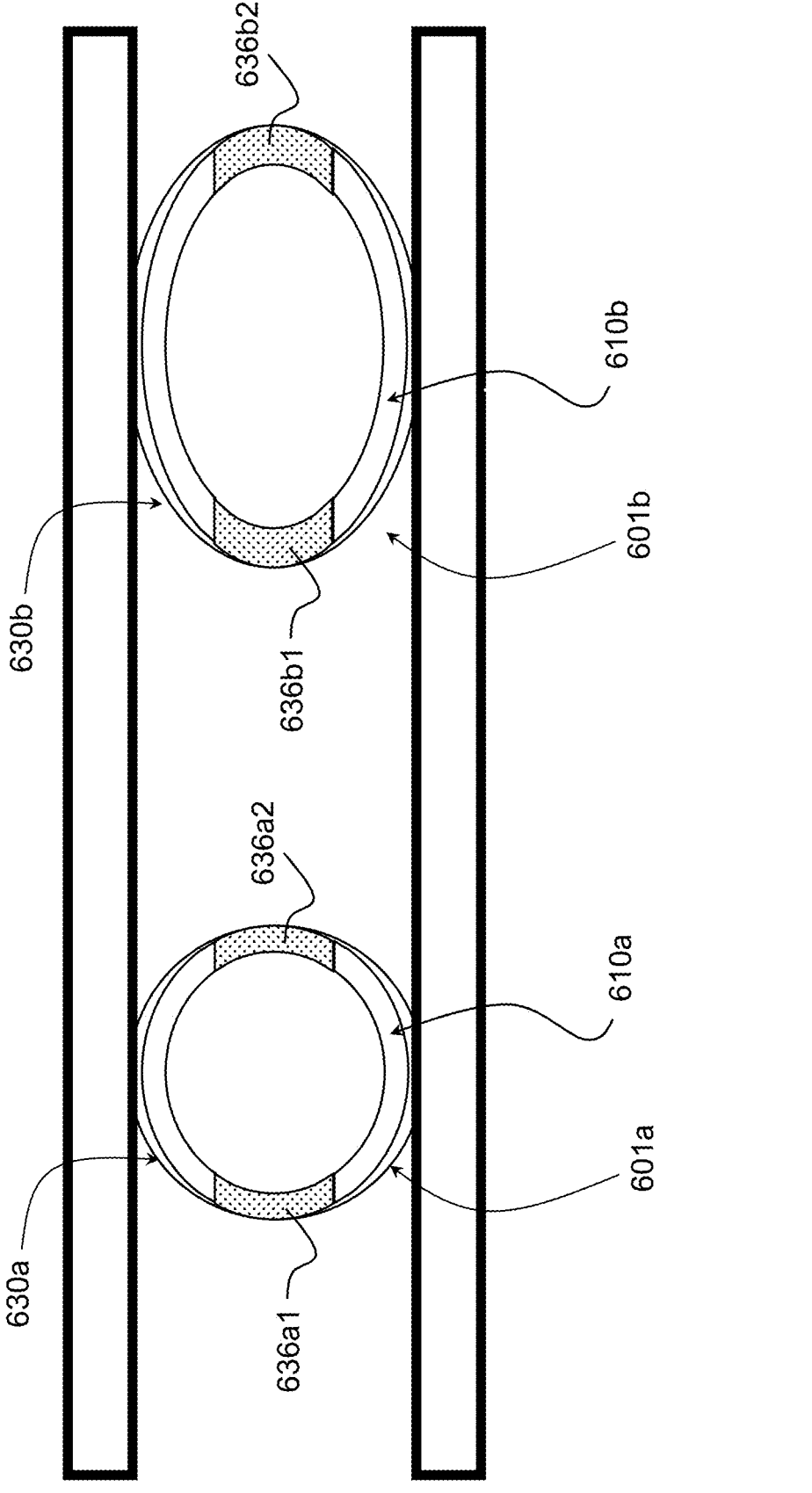
FIG. 12 is a schematic cross-section view of another two variations of a reversible occlusion device according to the present application.

With additional attention being drawn to FIG. 12, two examples of a reversible occlusion device are shown, generally designated 601a and 601b respectively. As opposed to the previously described occlusion devices, the reversible occlusion devices 601a and 601b have a generally spherical geometry, shown here in cross-section as a circle (601a) or as an oval (601b).

The reversible occlusion device 601a comprises a scaffold 610a formed with two openings and covered by a sheath 630a, such that the sheath 630a forms two membrane areas: an upstream membrane area 636a1, and a downstream membrane area 636a2. The occlusion device 601a is spherical, and its contact area with the lumen is minimal. Similarly, the reversible occlusion device 601b comprises a scaffold 610b formed with two openings and covered by a sheath 630b, such that the sheath 630b forms two membrane areas: an upstream membrane area 636b1, and a downstream membrane area 636b2. The occlusion device 601b is a spheroid having an oval cross-section, and its contact area with the lumen is slightly greater than the occlusion device 601a.

Both these occlusion devices 601a, 601b, have a considerably smaller form factor than the previously discussed occlusion devices (1, 101, 201, 301, 401, 501), and therefore may allow introduction of a plurality of such devices into the lumen in case one was already reopened, or malfunctioned. This is done without the needs to pull out the previous occlusion device.

Figure 11B:
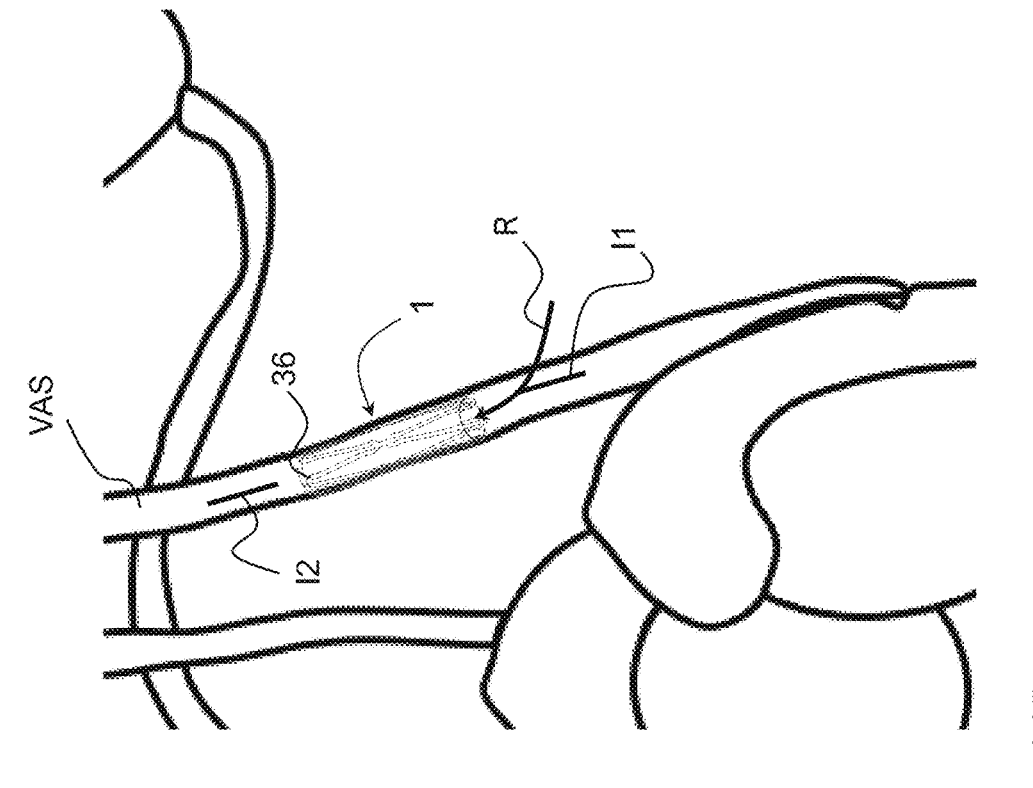
FIG. 11B is a schematic enlarged view of a portion of the diagram shown in FIG. 11A, including the reversible occlusion device.
Figure 11A:
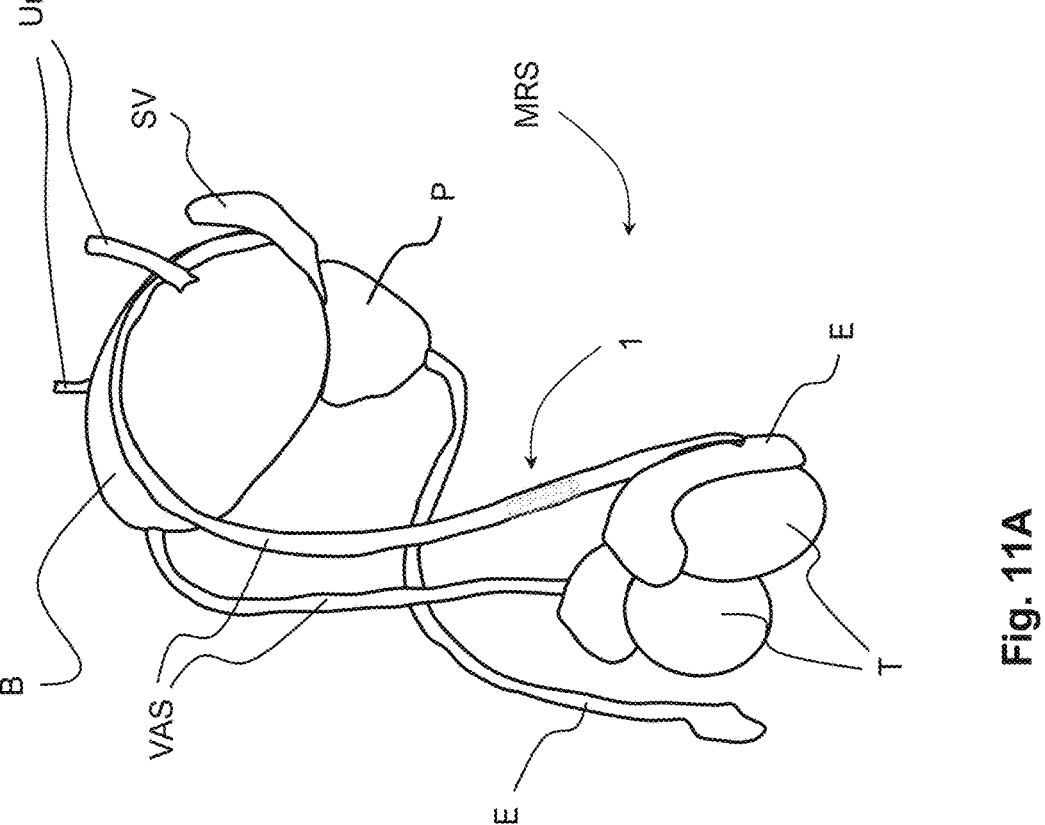
FIG. 11A is a schematic diagram of a male reproductive system in which the reversible occlusion device of FIGS. 1A and 1B is implemented.

Turning now to FIGS. 11A and 11B, any of the reversible occlusion devices 1, 101, 201, 301, 401, 501 & 601, may be used as a male contraceptive in a VAS occlusion procedure. In this specific example, the reversible occlusion device 1 is shown, but it should readily be understood that any of the other reversible occlusion devices may be used in a similar fashion.

The reversible occlusion device may be inserted into the lumen either percutaneously, or through an incision I1 in the Vas Deferens VAS, allowing insertion of a leading tube S (shown FIGS. 4A-4D), and the introduction of the reversible occlusion device 1, 101, 201, 301, 401, 501, into the VAS duct. In the event that sperm is released from the testes T into the VAS towards the urethra U, it will meet the reversible occlusion device 1, 101, 201, 301, 401, 501 and be blocked by the restricting element (either membrane 36, restricting elements 334, 444, or the plug 501), and will thus be prevented from reaching the urethra.

Following the introduction of the reversible occlusion device, if unblocking is desired (reversal procedure), it is possible to access the vas lumen 12 downstream of the reversible occlusion device 1, 101, 201, 301, 401, 501 (either percutaneously or through an incision), and introduce therethrough a perforation device 50 (as shown in FIGS. 5A-5C) to perforate the membrane 36, re-opening the reversible occlusion device 1, or an actuator, allowing to engage with the plunger 340, 440, respectively, and operate it to then actively open/close the reversible occlusion device. With regards to the reversible occlusion device 501, an extractor device (not shown) can be introduced through either incision I1 or I2, in order to extract the plug 510 from the housing 530.

Those skilled in the art to which this invention pertains will readily appreciate that numerous changes, variations, and modifications can be made without departing from the scope of the invention, mutatis mutandis.

The invention claimed is:

1. A reversible occlusion device configured for being introduced inside a lumen to selectively occlude said lumen, said reversible occlusion device comprising a docking unit configured for being docked in the lumen and having, at least when positioned the lumen, an upstream end associated with an upstream portion of the lumen, and a downstream end associated with a downstream portion of the lumen, and an inner volume extending between a first opening at said upstream end, and a second opening at said downstream end, said reversible occlusion device further comprising at least one restricting element configured for transitioning, at least once, between a first, closed position, in which said restricting element obstructs passage of material across said volume between said first opening and said second opening, and a second, open position, in which said restricting element allows passage of material across said volume between said first opening and said second opening, wherein in both said closed position and said open position, a peripheral portion of said restricting element is in contact with said docking unit, wherein said restricting element is in the form of a membrane having a variable thickness, wherein a peripheral portion of the membrane, located closer to the docking unit, has a first thickness t1, and wherein a central portion of the membrane, closer to the longitudinal axis of the reversible occlusion device, has a second thickness t2<t1.

2. The reversible occlusion device according to claim 1, wherein said membrane is a tearable membrane covering an opening of said at least one cavity, and wherein said tearable membrane is at least:
   a. sufficiently strong for obstructing passage of material across said opening; and
   b. sufficiently thin to allow perforation thereof in order to allow passage of material across said opening, when torn.

3. The reversible occlusion device according to claim 2, wherein the tearable membrane constitutes any one of the following:
   an extension of the docking unit; and
   a part of a sheath which is adhered and/or integrally formed with the docking unit.

4. The reversible occlusion device according to claim 2, wherein the tearable membrane is made of a thin sheet of material, which is configured for being torn by an external device.

5. The reversible occlusion device according to claim 2, wherein the docking unit further comprises at least one auxiliary opening arrangement which is mechanically biased for applying axial pressure on the tearable membrane.

6. The reversing apparatus for the reversible occlusion device of claim 1, comprising at least one working end configured for engaging with said restricting element for transitioning it at least from its first, closed position, to its second, open position, wherein the reversing apparatus is in the form of a perforation device comprising a housing and at least one spike formed with a pointed tip configured for puncturing a membrane, said spike being configured for displacing within the housing between at least a first, retracted position in which said tip is spaced $A_1$ distance a from a distal end of the housing and a second, extended position, in which said tip is spaced a distance $A_2$ from the distal end of the housing, wherein $A_2 < A_1$.

7. The reversing apparatus according to claim 6, wherein the perforation device comprises at least one cutting element laterally extending from said housing, said cutting element being configured, once the membrane is punctured by the tip of the spike, to cut at least a portion of the tearable membrane still attached to the scaffold.

8. The reversing apparatus according to claim 7, wherein said at least one cutting element constitutes part of a cutting and removal module, also configured for removing at least the cut portion of the membrane, cut by the cutting element.

9. A method for reopening a reversible occlusion device according to claim 1, when positioned within a lumen, the method comprising the steps of:
    a. introducing a dedicated device into said lumen; and
    b. within the lumen, using said dedicated device to transition said restricting element from said first, closed position to said second, open position.

10. The method according to claim 9, wherein step (b) is performed as any one or more of the following:
    i. tearing a restricting element;
    ii. directly or indirectly displacing a restricting element along said docking unit; and
    iii. removing a restricting element from the docking unit.

11. The method according to claim 10, wherein the method includes a step of introducing an additional reversible occlusion device into the lumen, to be placed in tandem with the opened reversible occlusion device.

12. The reversible occlusion device according to claim 1, further comprising a sheath at least partially covering a scaffold, whereby, when the reversible occlusion device is introduced into the lumen, the lumen is at least partially exposed to the volume of the docking unit.

13. The reversible occlusion device according to claim 1, wherein the reversible occlusion device is used as birth contraceptive, wherein the lumen is a genital lumen.

14. The reversible occlusion device according to claim 1, wherein the restricting element is configured to withstand an influx of fluid advancing through the lumen, and preventing this fluid from either entering, exiting or progressing through the docking unit.

15. The reversible occlusion device according to claim 1, wherein the docking unit is configured for being introduced into the lumen such that the restricting element is located in one of the following orientations:
    a downstream of an open end of the cavity, whereby the restricting element is configured for preventing fluid that enters the cavity from exiting from an opposite end of the docking unit;
    upstream of an open end of the cavity, whereby the restricting element is configured for preventing fluid from entering the cavity; and
    a point between the ends of the docking unit, thereby preventing fluid flow across at least a portion of the docking unit.

16. The reversible occlusion device according to claim 1, wherein the central portion of the membrane constitutes between 50%-80% of the membrane area.

17. The reversible occlusion device according to claim 1, wherein the width $t1$ is in the range of 40 μm-60 μm, while the width $t2$ is in the range of 60 μm-80 μm.

18. The reversible occlusion device according to claim 1, wherein the restricting element comprises at least one resilient portion/segment, and wherein the reversible occlusion device comprises a pressure arrangement configured for at least partially displacing within said docking unit, for transposing between:
    i. normally assuming a first, pressure position in which it applies pressure on said resilient portion, resulting in deformation of the resilient portion, closing off said aperture; and
    ii. assuming a second, release position, in which it applies less pressure on said resilient portion, thereby allowing the aperture of said restricting element to become opened.

19. The reversible occlusion system comprising a reversible occlusion device according to claim 6, and a reversing apparatus according to claim 14.

\* \* \* \* \*